United States Patent [19]

Vega-Noverola et al.

[11] Patent Number: 4,937,236
[45] Date of Patent: Jun. 26, 1990

[54] ANXIOLYTIC N-SUBSTITUTED BENZAMIDES

[75] Inventors: Armando Vega-Noverola; Jose M. P. Soto; Fernando P. Noguera; Jacinto M. Mauri, all of Barcelona; Robert G. W. Spickett, Tibidabo, all of Spain

[73] Assignee: Fordonal, S.A., Madrid, Spain

[21] Appl. No.: 445,487

[22] Filed: Dec. 4, 1989

Related U.S. Application Data

[63] Continuation of Ser. No. 217,646, Jul. 12, 1988, Pat. No. 4,877,780.

[30] Foreign Application Priority Data

Aug. 3, 1987 [GB] United Kingdom ............... 8718345

[51] Int. Cl.$^5$ ............................................. A61K 31/625
[52] U.S. Cl. ............................... 514/161; 514/299; 514/304; 514/305
[58] Field of Search ............... 514/161, 299, 304, 305

[56] References Cited

U.S. PATENT DOCUMENTS 4,820,715 4/1989 Monkovic et al. ............... 514/305

Primary Examiner—Richard A. Schwartz
Attorney, Agent, or Firm—Spencer & Frank

[57] ABSTRACT

A method of treating anxiety including administering to a person to be treated an effective amount of Compounds of the general formula:

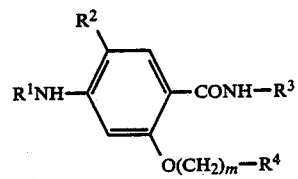

wherein the various substituents are defined hereinbelow have pharmacological properties rendering them useful as antiemetic agents with reduced undesirable side-effects or as anxiolytic agents. Various methods are described for their preparation involving formation of the amide link, etherification of the 2-hydroxy derivative, introducing the $R^5CH_2$ group on the N-unsubstituted azabicyclooctane or nonane or, for 4-amino compounds, by hydrolysing a 4-acylamino derivative.

12 Claims, No Drawings

ANXIOLYTIC N-SUBSTITUTED BENZAMIDES

This is a continuation of application Ser. No. 217,646 filed July 12, 1988, now U.S. Pat. No. 4,877,780.

This invention relates to new N-substituted benzamides, methods for their preparation, intermediates involved in these methods, compositions containing them and their use in medical treatment.

N-substituted benzamides have been shown to possess a number of pharmacological properties most of which are related to their ability to antagonize the central and peripheral effects of dopamine and/or facilitate the release of acetylcholine onto muscarinic receptors in the gastrointestinal smooth muscle. This had led to their successful clinical use as antiemetic and in the treatment of a wide range of gastrointestinal disorders of somatic, psychosomatic and iatrogenic origin. European Pat. Appl. 099789 A1 disclosed a series of new benzamides of which N-(1-azabicyclo[2.2.2]oct-3-yl)-2-methoxy-4-amino-5-chlorobenzamide (INN, Zacopride) is the most important as potent antiemetic. In contrast to other known antiemetic compounds as Metoclopramide (N-[2-(diethylamino)ethyl]-2-methoxy-4-amino-5-chlorobenzamide, the compounds of the above mentioned Patent, do not present antidopaminergic effects which are associated with extrapyramidal symptoms and side effects related to hyperprolactinemia. However, the benzamides of the above mentioned Europ. Pat. Appln. present a spectrum of antiemetic activity more limited than Metoclopramide as they are not active in tests such as CuSO4-induced vomiting in the dog.

We have now found that the introduction of new groups in the 2 position of the benzamide ring, provides new compounds that present not only a wide spectrum of antiemetic activity, but also a lack of antidopaminergic side effects.

Consequently the new N-substituted benzamides of the invention represent an important advance in respect to Metoclopramide and related compounds as those described in the above patent.

Accordingly, the present invention provides a compound of the formula:

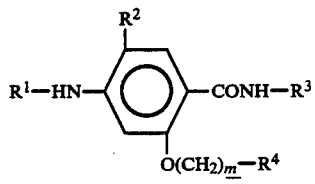

wherein $R^1$ represents a hydrogen atom or a lower alkyl or acetyl group, $R^2$ represents a halogen atom (preferably chlorine or bromine), $R^3$ represents a group of formula:

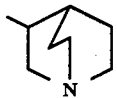

-continued

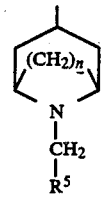

in which $R^5$ represents a hydrogen atom or a phenyl or a non-aromatic cyclic ether group (preferably tetrahydrofuryl, or 1,3-dioxolanyl), and n represents 2 or 3, $R^4$ represents a $C_3$–$C_6$ cycloalkyl, cyclohexenyl (preferably 3-cyclohexenyl), lower alkoxy, trifluoromethyl, tetrahydrofuryl, 1,3-dioxolanyl or phenoxy group, m represents an integer from 0 to 4 with the proviso that when m is 0, $R^4$ is only a $C_3$–$C_6$ cycloalkyl or tetrahydrofuryl group, and pharmacologically-acceptable acid addition salts thereof.

The qualification "lower" as applied herein to alkyl and alkoxy groups means that the group in question contains at most 6 (and preferably not more than 4) carbon atoms. In the compounds of the invention of general formula I, when $R^5$ represents a non-aromatic cyclic ether group, it means that $R^5$ contains no aromatic ring system but contains one ring system having from 2 to 6 ring carbon atoms and one or two ring oxygen atoms (e.g. tetrahydrofurane, tetrahydropyrane, 1,3-dioxolane and 1,4 dioxane).

Of the N-substituted benzamides of general formula I those wherein $R^1$ represents a hydrogen atom, $R^2$ represents a chlorine atom, $R^3$ represents a group of formula II, $R^4$ represents a cyclopropyl or lower alkoxy group and m represents 1 or 2, are of paticular importance. Preferred compounds are N-(1-azabicyclo[2.2.2]oct-3-yl)-2-cyclopropylmethoxy-4-amino-5-chlorobenzamide and N-(1-azabicyclo[2.2.2]oct-3-yl)-2-methoxyethoxy-4-amino-5-chlorobenzamide. Suitable compounds are those wherein $R^1$ represents hydrogen or a $C_{1-6}$ alkyl group, $R^4$ represents a $C_{3-6}$ cycloalkyl, $C_{1-6}$ alkoxy, trifluoromethyl, tetrahydrofuryl, 1,3-dioxolanyl or a phenoxy group and $R^2$, $R^3$ and m are as defined above.

According to a feature of the present invention, the compounds of the invention are prepared by the process which comprises reacting a reactive derivative of a benzoic acid of the general formula:

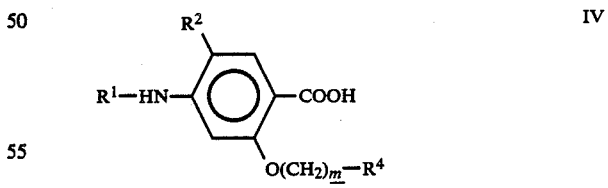

(wherein the various symbols are as hereinbefore defined) with an amine of the general formula V:

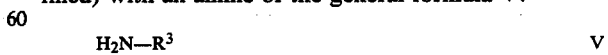

wherein $R^3$ is as hereinbefore defined. The reactive derivative of the said benzoic acid may be, for example, a halide (preferably chloride), an alkyl ester (preferably methyl ester), an anhydride or a mixed anhydride. The benzoic acid of general formula IV in which $R^4$ represents a $C_3$–$C_6$ cycloalkyl group is novel and represents a further aspect of this invention. It is prepared by condensation of a lower alkyl ester of the corresponding 2-hydroxy acid with the appropriate halogen derivative, and finally, hydrolysing the carboalkoxy grup to carboxy e.g. with alkali.

The reaction of IV with V is preferably carried out in the presence of an inert organic solvent, for example benzene, toluene, chloroform, tetrahydrofuran, N,N-dimethylformamide or dioxan, at a temperature between −5° and 120° C.

Halides of the benzoic acids of general formula IV can be prepared by reaction of the acid with thionyl chloride or a phosphorus halide in the presence of an inert organic solvent such as benzene, toluene or a halogenated hydrocarbon. Mixed anhydrides of the benzoic acids of general formula IV can be prepared by the reaction of the acid with, for example, an alkyl chloroformate in the presence of an organic nitrogen-containing base, e.g. triethylamine, in an inert organic solvent, e.g. tetrahydrofuran, N,N-dimethylformamide or methylene chloride and at a temperature between −20° and +25° C. Esters and anhydrides of the benzoic acids of formula IV, which may be employed as starting materials in the aforementioned process, can be prepared from the benzoic acids by methods known per se.

In the preparation of those compounds of general formula I wherein the symbol $R^1$ is hydrogen it is sometimes advisable to use as starting material corresponding compounds in which the amino group is protected by an acyl group, the acyl protecting group preferably being acetyl, chloroacetyl, trifluoroacetyl or phthaloyl. After the reaction the N-acylated intermediate products are subjected to alkaline hydrolysis to give the corresponding compounds of general formula I in which $R^1$ represents a hydrogen atom. When $R^5$ is other than a non aromatic cyclic ether group, and $R^4$ is a $C_3$-$C_6$ cycloalkyl, cyclohexenyl or a lower alkoxy group, the N-acylated intermediate products can also be subjected to acid hydrolysis. Alkaline hydrolysis of the N-acylated compound is preferably carried out at a temperature between 20° and 90° C. with sodium or potassium hydroxide in an aqueous-alcoholic solution, while acid hydrolysis is preferably carried out by heating with dilute hydrochloric acid at the boiling point of the reaction mixture.

The compounds of the invention, in which $R^3$ is a group of formula III as defined above, can also be prepared from an N-unsubstituted compound of formula:

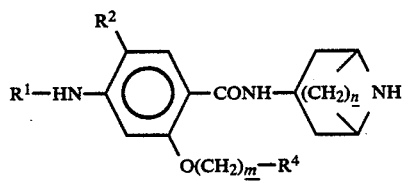

VI

wherein the various symbols are as hereinbefore defined.

The compound VI which is novel and represents a further aspect of this invention, is prepared by subjecting the corresponding N-benzyl compound to catalytic hydrogenolysis in a solvent such as a $C_1$-$C_6$ alcohol in the presence of a noble metal catalyst, e.g. palladium or platinum, which may be absorbed on an inert support such as carbon or barium sulphate, in the presence of hydrogen at normal or elevated pressure and at temperatures between room temperature and 100° C. The compound VI in which $R^1$ is other than acetyl group can also be prepared by hydrolysing the corresponding lower alkoxy carbonyl ester, preferably an ethoxycarbonyl compound of formula VII:

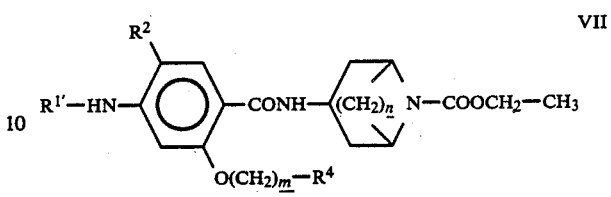

VII (wherein $R1'$ is a hydrogen atom or a lower alkyl group and the other symbols are as hereinbefore defined) with alkali e.g. sodium or potassium hydroxide in an organic solvent, for example ethanol or isopropanol, at the boiling point of the solvent. The compound VI may then be reacted with an appropriate halide or sulphonate of structure:

$$W-CH_2-R^5 \qquad VIII$$

where W is a halogen atom or a sulphonate such as a methanesulphonate, p-toluenesulphonate or benzenesulphonate group and $R^5$ is as defined above, in the presence of a base such as sodium or potassium carbonate or sodium or potassium bicarbonate, in an organic solvent such as toluene, dioxane or methyl isobutyl ketone at a temperature between 40° and 140° C.

The compounds of general formula I can also be prepared, according to a further feature of the invention, by the direct reaction of a benzoic acid of general formula IV with an amine of general formula V, preferably in the presence of an appropriate dehydrating agent. Such agents include silicon tetrachloride, a mono-, di- or trialkylsilyl chloride, titanium tetrachloride, N,N'-dicyclohexyl-carbodiimide, carbonyl diimidazole, thionyl chloride, sulphur trioxide in dimethyl sulphoxide, toluene-p-sulphonyl chloride, acetone dimethyl acetal or a polymeric dehydrating agent. The reaction can be carried out in an inert organic solvent, e.g. methylene chloride, acetone, pyridine, ethyl acetate or dioxan, at a temperature between 20° and 110° C. The compounds of the invention of formula I can also be prepared from the hydroxy derivative of formula IX:

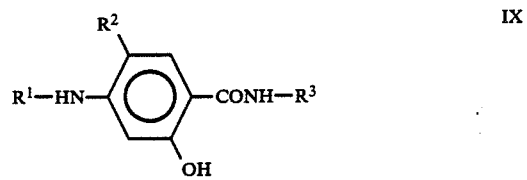

IX

wherein the various symbols are as hereinbefore defined, by reaction with a halogen derivative of formula X:

$$Z-(CH_2)_m-R^4 \qquad X$$

wherein Z is chloro, bromo or iodo and $R^4$ and m are as hereinbefore defined. The reaction is preferably carried out in an organic solvent such as methyl isobutyl ketone, N,N-dimethylformamide, dioxane, or toluene at a temperature between 40° and 140° C. and in the presence of an organic or inorganic base such as sodium or potassium carbonate.

The intermediate amines of formula V wherein $R^3$ is III can give alpha and beta isomers according to whether the amino group is in the axial or equatorial position. Both isomers can be prepared by the method disclosed in Eur. J. Med. Chem. 1984, 19, p. 105–110 and J. Heterocyclic Chem. 19, 485 (1982).

The benzoic acids starting materials IV, in which $R^4$ is other than $C_3$–$C_6$ cycloalkyl, used in the preparation of the compounds of the invention, are prepared according to the general methods described, for example, in GB 1,507,462, GB 1,088,581 and GB 1,019,781.

The N-substituted benzamides of general formula I can be converted by methods known per se into acid addition salts, for example by reaction of the basic compounds with acids in appropriate solvents, for example alcohols, dialkyl ketones or ethers. Suitable acid addition salts are those derived from inorganic acids, for example the hydrochlorides and sulphates, and organic acids, for example the fumarates, acetates, succinates and citrates. Also included within the scope of the invention are N-oxides and pharmaceutically acceptable quaternary ammonium salts of N-substituted benzamides of general formula I in which the cyclic nitrogen atom is quaternised by reaction for example with a $C_1$–$C_6$ alkyl halide or sulphate. The N-substituted benzamides of general formula I have potent gastrokinetic and antiemetic activities and block 5-HT$_3$ receptors in the absence of dopamine antagonist effects.

The pharmacological screening of compounds to optimise these effects was carried out using the following tests:

(1) Stimulation by 5-HT of 5HT$_3$ receptors located in vagal afferent fibres produces a fall in heart rate and blood pressure in the anaesthetized rat (Bezold-Jarisch reflex). (Fozard, J. R. & Host, M. Br. J. Pharmacol. (1982) 77: 520P)

(2) Cis-platinum induced emesis in the dog administering compounds by oral or intravenous route. (Gylys, J. A., Dora, K. M. & Buyniski J. P. Res. Comm. Chem. Pathol. Pharmacol. (1979)23: 61–68).

(3) CuSO$_4$—induced emesis in the dog administering compounds by subcutaneous or intravenous route. (Kayashima, N., Tanaka, M., Iwasaki, M. & Hayama, T. Japan J. Pharmacol. (1978)28: 775–781).

(4) Apomorphine-induced emesis in the dog administering compounds by subcutaneous or intravenous route. (Prala, J. J., High, J. P., Hasses, G. L., Burke, J. C. and Craven, B. N. J. Pharmac. Exp. Therap. 127, 55–65, 1959).

(5) Stomach emptying in the rat, administering compounds by oral route. (Jacoby, H. I., and Brodie, D. A. Gastroenterol. 52, 676–684, 1967).

The N-substituted benzamides of general formula I were compared with Metoclopramide (N-[2-diethylamino) ethyl]-2-methoxy-4-aminio-5-chlorobenzamide) and Zacopride (N-(1-azabicyclo[2.2.2]oct-3-yl)-2-methoxy-4-amino-5-chloro-benzamide) and were shown to have advantageous antiemetic profiles due to the presence of the new substituents in position 2 of the benzamide group.

As shown Table I, compounds of general formula I, produce a potent inhibition of the Bezold-Jarisch reflex in the rat at a dosage level 100–800 times lower than Metoclopramide. This activity has been recently related to the ability of antagonising the cytotoxic drug-induced vomiting. In fact, all of them inhibit the cisplatin-induced vomiting in the dog and particularly compound 1 shows a similar potency to Zacopride.

Metoclopramide decreases the number of emetic episodes in the CuSO$_4$-induced vomiting in the dog, the new compounds have significant activity in this test, whereas Zacopride is totally inactive.

Like Zacopride, the new compounds lack antiemetic activity in the apomorphine-induced vomiting in the dog whereas Metoclopramide is a very active compound in this test. All of them show a good prokinetic activity in the gastric emptying of glass beads in the rat.

In conclusion, the present results clearly indicate that N-substituted benzamides of general formula I have a broader antiemetic spectrum than Zacopride without the dopamine antagonistic activity of Metoclopramide, and therefore without the potential for associated extrapyramidal side effects.

TABLE I

| COMPOUND | BEZOLD-JARISCH REFLEX IN THE RAT (ID$_{50}$; μg/kg i.v.) | CISPLATIN-INDUCED VOMITING IN THE DOG No EMETIC EPISODES 0.03 mg/kg i.v. | CISPLATIN-INDUCED VOMITING IN THE DOG (% inhibition) 0.1 mg/kg p.o. | C$_4$SO$_4$-INDUCED VOMITING IN THE DOG 1 mg/kg i.v. No EMETIC EPISODES (% Inh.) | APOMORPHINE-INDUCED VOMITING IN THE DOG 1 mg/kg i.v. % Protected animals | GASTRIC EMPTYING IN THE RAT MAX.EMPT. − DRUG EMPT. / MAX.EMPT. − VEHICLE EMPT. × 100  0.01 mg/kg p.o. | 1.0 mg/kg p.o. |
|---|---|---|---|---|---|---|---|
| METOCLOPRAMIDE | 330 | 69 (1 mg/kg i.v.) | 85 (3 mg/kg p.o.) | 60 | 100 | 0 | 42 |
| ZACOPRIDE | 0.21 | 92 | 88 | 0 | 0 | 51 | 77 |
| Compound 11 | 0.42 | 81 | 0 | 24 | 0 | 60 | 68 |
| Compound 1 | 0.56 | 88 | 85 | 40 | 0 | 55 | 85 |
| Compound 23 | 0.63 | 31 | 53 | 30 | 0 | 13 | 61 |
| Compound 16 | 2.6 | 53 | 61 | 45 | 0 | 32 | 71 |

Compound 11: N-(1-azabicyclo[2.2.2]oct-3-yl)-2-methoxyethoxy-4-amino-5-chlorobenzamide
Compound 1: N-(1-azabicyclo[2.2.2]oct-3-yl)-2-cyclopropylmethoxy-4-amino-5-chlorobenzamide
Compound 23: N-(8-methyl-8-azabicyclo[3.2.1]oct-3β-yl)-2-methoxyethoxy-4-amino-5-chlorobenzamide
Compound 16: N-(8-methyl-8-azabicyclo[3.2.1]oct-3β-yl)-2-cyclopropylmethoxy-4-amino-5-chlorobenzamide The N-substitued benzamides of general formula I also present analgesic, anxiolytic and antimigraine activity as a consequence of their anti 5-HT$_3$ activity. The present invention also provides pharmaceutical compositions which comprise, as active ingredient, at least one compound of general formula I, or a pharmacologically acceptable salt in association with a pharmaceutically acceptable carrier or diluent. The active ingredient may comprise 0.0001% to 99% by weight, preferably 0.001% to 90% by weight of the composition depending upon the nature of the formulation and whether further dilution is to be made prior to application. Preferably the compositions are made up in a form suitable for oral, topical, percutaneous or parenteral administration.

The pharmaceutically acceptable carriers or diluents which are admixed with the active compound, or compounds or salts of such compounds, to form the compositions of this invention are well known per se and the actual excipients used depend inter alia on the intended method of administering the compositions. Compositions of this invention are preferably adapted for administration per os. In this case, the composition for oral administration may take the form of tablets, capsules, lozenges or effervescent granules or liquid preparations, such as mixtures, elixirs, syrups or suspensions, all containing one or more compounds of the invention; such preparations may be made by methods well known in the art.

The diluents which may be used in the preparation of the compositions include those liquid and solid diluents which are compatible with the active ingredient, together with colouring or flavouring agents, if desired. Tablets or capsules may conveniently contain between 0.1 and 20 mg of active ingredient or the equivalent amount of an acid addition salt thereof.

The liquid compositions adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in water or an appropriate parenteral injection fluid.

A further aspect of the present invention provides a method for treating various gastro-intestinal disorders including vomiting in mammals including man by administering an effective amount of a compound or salt of formula I, suitably using compositions and administration routes described above. Effective doses are normally in the range of 0.1–100 mg of active ingredient per day.

In another aspect of the invention, the compounds may be mixed with active anti-acid and anti-ulcer agents (excluding anti-cholinergic agents) for oral or, in appropriate cases, for parenteral use.

The following Examples illustrate the preparation of compounds of the present invention.

EXAMPLE 1

To a solution of 2-cyclopropylmethoxy-4-amino-5-chlorobenzoic acid (3.2 g; 0.0134 moles) in pyridine (15 ml), a solution of 3-aminoquinuclidine dihydrochloride (2.5 g; 0.0125 moles) and sodium hydroxide (0.5 g; 0.0125 moles) in water (15 ml) was added. To the resulting solution, N,N'-dicyclohexyl-carbodiimide (3.1 g; 0.0146 moles) was added and the mixture stirred at room temperature for 20 hours. An additional amount of N,N'-dicyclohexyl-carbodiimide (3.1 g; 0.0146 moles) was added and the mixture stirred for a further 24 hours. The insoluble solid was filtered off, washed with water and the solvent removed in vacuo at a temperature between 30° and 45° C. The solid residue was taken up in water, made alkaline with sodium hydroxide and a solid precipitated which was filtered off and dried to give N-(1-azabicyclo[2.2.2]oct-3-yl)-2-cyclopropylmethoxy-4-amino-5-chlorobenzamide (4.1 g) M.p. 183°–185° C. after recrystallisation from acetonitrile.

EXAMPLE 2

Triethylamine (1.6 ml; 0.0113 moles) and ethyl chloroformate (1.15 ml; 0.0113 moles) were added succesively to a stirred solution of 2-methoxyethoxy-4-amino-5-chlorobenzoic acid (2.8 g; 0.0113 moles) in methylene chloride (125 ml) whilst maintaining the temperature between −5° and −10° C. After stirring at this temperature for 2 hours, a solution of 3$\beta$-amino-8-methyl-8-azabicyclo[3.2.1]octane(1.6 g; 0.0113 moles) in methylene chloride (10 ml) was added, the temperature was maintained at −5° to −10° C. for 1 hour and then allowed to reach room temperature overnight. The reaction mixture was washed with water, aqueous sodium hydroxide solution, and then with water. After drying (Na$_2$SO$_4$) the solvent was removed in vacuo to give an oil which was disolved in ethanol and reacted with the stoichiometric amount of fumaric acid. The boiling solution was diluted with isopropanol and on cooling N-(8-methyl-8-azabicyclo[3.2.1]oct-3$\beta$-yl)-2-(2-methoxyethoxy)-4-amino-5-chlorobenzamide acid fumarate (1.1 g) crystallized, m.p. 211°–213° C. (d).

EXAMPLE 3

A mixture of N-(8-azabicyclo[3.2.1]oct-3$\beta$-yl)-2-cyclopropylmethoxy-4-amino-5-chlorobenzamide (2.3 g; 0.007moles), 2-bromomethyl-1,3-dioxolane (1.3 g; 0.0077 moles), potassium carbonate (1 g; 0.007 moles) and acetonitrile (100 ml) was boiled under reflux for 48 hours after which, an additional amount of 2-bromomethyl-1,3-dioxolane (0,5 g; 0.003 moles) was added. The reaction mixture was boiled under reflux for other 48 hours and then, the solvent was removed in vacuo, the residue treated with water and extracted with methylene chloride.

The organic solution was dried (Na$_2$ SO$_4$), decolorized with charcoal and the solvent removed in vacuo to give crude N-[8-[2-(1,3-dioxolanyl)methyl]-8-azabicyclo[3.2.1]oct-3$\beta$-yl-]2-cyclopropylmethoxy-4-amino-5-chlorobenzamide (2.2 g). This compound was purified by column chromatography with silica gel and methanol:ammonium hydroxide (100:1.5) as solvent, m.p. 125°–127° C.

EXAMPLE 4

A suspension of N-(1-azabicyclo[2.2.2]oct-3-yl)-2-hydroxy-4-acetamido-5-chlorobenzamide (6.75 g; 0.02 moles) (m.p. of hydrochloride 315°–317° C. (d)), potassium carbonate (2.76 g; 0.02 moles), 91.5% bromomethylcyclopropane (3.54 g; 0.024 moles) and methyl isobutyl ketone (40 ml) was boiled under reflux for 48 hours. After cooling, the reaction mixture was washed with water, 1N sodium hydroxide aqueous solution and again with water. The organic solution was dried (Na$_2$ SO$_4$), decolorized with charcoal and the solvent removed in vacuo to give crude N-(1-azabicyclo[2.2.2]oct-3-yl)-2-cyclopropylmethoxy-4-acetamido-5-chlorobenzamide (6.6 g) as an oil, which was crystallized from acetonitrile, m.p.211°–213° C. (d).

EXAMPLE 5

A solution of N-(1-azabicyclo[2.2.2.]oct-3-yl)-2-cyclopropylmethoxy-4-acetamido-5-chlorobenzamide (3.9 g; 0.01 mol), sodium hydroxide (2 g; 0.05 moles), ethanol (50 ml) and water (20 ml), was boiled under reflux for 2 hours. Then the ethanol was removed in vacuo, the residue diluted with water, and the insoluble solid filtered off and washed thoroughly with water. The obtained N-(1-azabicyclo[2.2.2]oct-3-yl)-2-cyclopropylmethoxy-4-amino-5-chlorobenzamide (3.2 g) was purified by recrystallization from acetonitrile, m.p. 183°–185° C.

EXAMPLE 6

To a solution of N-(1-azabicyclo[2.2.2]oct-3-yl)-2-cyclopropylmethoxy-4-amino-5-chlorobenzamide (3.5 g; 0.01 mol) in acetone (200 ml), iodomethane (2.8 g; 0.02 moles) was added and the resulting mixture stirred to room temperature for 20 hours. The precipitated solid was collected, washed with acetone and dried to give N-(1-azabicyclo[2.2.2]oct-3-yl)-2-cyclopropylmethoxy-4-amino-5-chlorobenzamide methyl iodide (3.9 g), m.p. 274°–276° C. (d) (after recrystallisation from a mixture of acetonitrile and water).

EXAMPLE 7

To a solution of N-(1-azabicyclo[2.2.2]oct-3-yl)-2-cyclopropylmethoxy-4-acetamido-5-chlorobenzamide (2.6 g; 0.007 moles) in acetic acid (20 ml), 30% hydrogen peroxide (1.8 ml) was added and the resulting solution was stirred at 80° C. for 15 hours. The solvent was removed in vacuo, the residue was treated with water, alcalinized with sodium hydroxide aqueous solution, saturated with sodium chloride and extracted with methylene chloride. The organic solution was dried ($Na_2SO_4$), the solvent removed in vacuo and the residual yellow solid treated with diethyl ether and collected. After washing with acetonitrile and diethyl ether, N-(1-azabicyclo[2.2.2]oct-3-yl)-2-cyclopropylmethoxy-4-acetamido-5-chlorobenzamide N-oxide was obtained as a white solid, which was dried at 50° C. to give 1.4 g; m.p. 234°–236° C. (d).

The compounds of general formula I included in the following Tables II and III were prepared according to the processes disclosed in Examples 1 to 5 as indicated.

TABLE II

[Structure: $R^1$-HN-phenyl ring with $R^2$ substituent and $O(CH_2)_m$-$R^4$ substituent, connected via CONH to azabicyclic ring]

| No | $R^1$ | $R^2$ | $R^4$ | m | Method Example | Base/Salt form | m.p. °C. |
|---|---|---|---|---|---|---|---|
| 1 | H | Cl | cyclopropyl | 1 | 1,5 | Base | 183–185 |
| 2 | $CH_3$ | " | " | " | 1 | ClH—$H_2O$ | 254–256 (d) |
| 3 | CO—$CH_3$ | " | " | " | 1,4 | Base | 211–213 (d) |
| 4 | H | " | cyclohexyl | " | 1 | " | 165–167 |
| 5 | " | " | " | 2 | 1 | ClH | 283–285 (d) |
| 6 | " | " | cyclopentyl | 0 | 1 | ClH.½$H_2O$ | 160–197 |
| 7 | " | " | tetrahydrofuryl | " | 1 | Base | 189–191 |
| 8 | " | " | " | 1 | 1 | " | 167–169 |
| 9 | " | " | tetrahydrofuryl | " | 1 | ClH.½$H_2O$ | 197–201 |
| 10 | " | " | " | 2 | 1 | ClH | 259–61 (d) |
| 11 | " | " | $OCH_3$ | " | 1 | Base | 166–168 |

TABLE II-continued

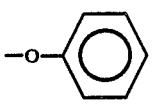

| No | R¹ | R² | R⁴ | m | Method Example | Base/Salt form | m.p. °C. |
|---|---|---|---|---|---|---|---|
| 12 | " | " | —O—C₆H₅ (phenoxy) | " | 1 | ClH.½H₂O | 232–234 |
| 13 | " | " | CF₃ | 1 | 1 | ClH.H₂O | 290–292 (d) |
| 14 | " | " | cyclohexenyl | " | 1 | Base | 173–175 |
| 15 | " | " | 1,3-dioxolanyl | " | 1 | " | 88–120 |

TABLE III

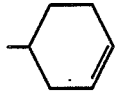

| No | R¹ | R² | R⁴ | R⁵ | m | n | Method Example | Base/Salt form | m.p. °C. |
|---|---|---|---|---|---|---|---|---|---|
| 16 | H | Cl | cyclopropyl | H | 1 | 2 | 1,2 | Base;β-isomer | 195–197 |
| 17 | " | " | " | C₆H₅ | " | " | 1,2 | Base;β-isomer | 174–176 |
| 18 | " | " | " | 1,3-dioxolanyl | " | " | 1,3 | Base;β-isomer | 125–127 |
| 19 | " | " | " | H | " | 3 | 1,2 | Base;β-isomer | 198–203 |
| 20 | " | " | " | tetrahydrofuryl | " | 2 | 1,3 | C₄H₄O₄(*) β-isomer | 189–191 |
| 21 | " | " | cyclopentyl | C₆H₅ | 0 | " | 1,2 | Base;β-isomer | 191–193 |
| 22 | " | " | OCH₃ | " | 2 | " | 1,2 | Base;β-isomer | 196–198 |
| 23 | " | " | " | H | " | " | 1,2 | C₄H₅O₄;β-isomer | 211–213 |
| 24 | " | " | " | " | " | 3 | 1,2 | C₄H₅O₄;β-isomer | 171–173 (d) |

The following Examples illustrate pharmaceutical compositions according to the present invention and procedures for their preparation

EXAMPLE 8

50,000 Tablets each containing 1 mg of N-(1-azabicyclo[2.2.2]oct-3-yl-2-cyclopropyl methoxy-4-amino-5-chlorobenzamide were prepared from the following formulation:

N-(1-azabicyclo[2.2.2]oct-3-yl)-2-cyclopropylmethoxy-4-amino-5-chlorobenzamide: 50 g
microcrystalline cellulose: 950 g
lactose spray dried: 4950 g
carboxymethyl starch: 200 g
sodium stearyl fumarate: 50 g
colloidal silicon dioxide: 50 g

Procedure

All the powders were passed through a screen with aperture of 0.6 mm, then mixed in a suitable mixer for 20 minutes and compressed into 125 mg tablets using 6 mm circular and flat bevelled punches. The disintegration time of the tablets was about 60 seconds.

EXAMPLE 9

2,000 Bottles (125 ml volume) each containing a solution of 25 mg of N-(1-azabicyclo[2.2.2]oct-3-yl-2-cyclopropylmethoxy-4-amino-5-chlorobenzamide were prepared as follows:

N-(1-azabicyclo[2.2.2]oct-3-yl-2-cyclopropylmethoxy-4-amino-5-chlorobenzamide: 50 g
sorbitol: 120000 g
sorbic acid: 250 g
citric acid: 250 g
distilled water q.s.: 250 liters
flavouring agent: q.s.

Procedure

The N-(1-azabicyclo[2.2.2]oct-3-yl-2-cyclopropylmethoxy-4-amino-5-chlorobenzamide and the sorbic acid were dissolved in 150 liters of water and then the sorbitol, citric acid and flavouring agent were added with stirring until dissolution. The mixture was diluted to 250 liters into 125 ml bottles using an appropriate filling machine.

EXAMPLE 10

10,000 Ampoules each containing 0.5 mg of N-(1-azabicyclo[2.2.2]oct-3-yl-2-cyclopropylmethoxy-4-amino-5-chlorobenzamide were prepared from the following formulation:

N-(1-azabicyclo[2.2.2]oct-3-yl-2-cyclopropylmethoxy-4-amino-5-chlorobenzamide: 5 g
sodium chloride: 250 g
lactic acid: 7 g
1N Sodium hydroxide aqueous solution: q.s. to pH=3
Water injectable grade q.s.: 50 liters

Procedure

The N-(1-azabicyclo[2.2.2]oct-3-yl-2-cyclopropylmethoxy-4-amino-5-chlorobenzamide, the lactic acid and the sodium chloride were dissolved in 40 liters of water. The resulting solution was neutralised to pH=3 with the sodium hydroxide solution, diluted to 50 liters, then passed through a bacteria-retaining filter and filled under sterile conditions into 5 ml glass ampoules in known manner.

EXAMPLE 11

5,000 Suppositories each containing 1 mg of N-(1-azabicyclo[2.2.2]oct-3-yl-2-cyclopropylmethoxy-4-amino-5-chlorobenzamide, were prepared as follows:

N-(1-azabicyclo[2.2.2]oct-3-yl-2-cyclopropylmethoxy-4-amino-5-chlorobenzamide: 5 g
theobroma oil: 9995 g

Procedure

The theobroma oil was melted and the active compound suspended in it. The mixture was then poured into appropriate suppository moulds to make 2.0 g suppositories.

EXAMPLE 12

100,000 Capsules each containing 1 mg of N-(1-azabicyclo[2.2.2]oct-3-yl-2-cyclopropylmethoxy-4-amino-5-chlorobenzamide were prepared as follows:

N-(1-azabicyclo[2.2.2]oct-3-yl-2-cyclopropylmethoxy-4-amino-5-chlorobenzamide: 100 g
lactose: 10500 g
corn starch: 9000 g
colloidal silicon dioxide: 200 g
magnesium stearate: 200 g

Procedure

All the powders, previously passed through a screen with an opening of 0.6 mm, were mixed for 20 minutes and distributed into 100,000 capsules of appropriate size using a filling machine.

We claim:

1. A method of treating anxiety which comprises administering to a patient suffering from or expected to suffer from anxiety disorders an effective amount of a compound of formula I or a pharmacologically acceptable salt or N-oxide thereof as defined below:

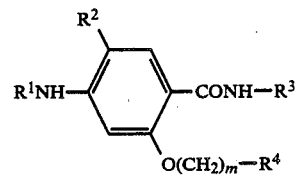

wherein $R^1$ represents hydrogen, a $C_{1-6}$ alkyl group or an acetyl group;
$R^2$ represents halogen;
$R^3$ represents a group of the formula:

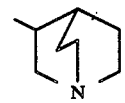

or

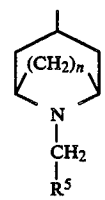

wherein $R^5$ represents hydrogen or a phenyl or non-aromatic cyclic ether group and n is 2 or 3;

$R^4$ represents a $C_{3-6}$ cycloalkyl, cyclohexenyl, $C_{1-6}$ alkoxy, trifluoromethyl, tetrahydrofuryl, 1,3-dioxolanyl or phenoxy group;

m is 0, 1, 2, 3 or 4 with the proviso that when m is 0, $R^4$ is only a $C_{3-6}$ cycloalkyl or tetrahydrofuryl group; or a pharmacologically acceptable acid addition salt, quaternary ammonium salt, or N-oxide thereof.

2. The method set forth in claim 1, wherein said compound of formula I is N-(1-azabicyclo[2.2.2]oct-3-yl)-2-cyclopropylmethoxy-4-amino-5-chloro-benzamide.

3. The method set forth in claim 1, wherein said compound of formula I is N-(1-azabicyclo[2.2.2]oct-3-yl)-2-(cyclopentyloxy)-4-amino-5-chloro-benzamide.

4. The method set forth in claim 1, wherein in said compound of formula I, $R^1$ represents hydrogen or a $C_{1-16}$ alkyl group, $R^4$ represents a $C_{3-6}$ cycloalkyl, $C_{1-6}$ alkoxy, trifluoromethyl, tetrahydrofuryl, 1,3-dioxolanyl or a phenoxy group and $R^2$, $R^3$ and m are as defined in claim 1.

5. The method set forth in claim 1, wherein in said compound of formula I, $R^1$ is hydrogen.

6. The method set forth in claim 1, wherein in said compound of formula I, $R^2$ is chlorine.

7. The method set forth in claim 1, wherein in said formula or I, $R^3$ is a group of formula II.

8. The method set forth in claim 1, wherein in said compound of formula I, $R^3$ is a group of formula III wherein n is 2.

9. The method set forth in claim 8, wherein $R^5$ is hydrogen.

10. The method set forth in claim 1, wherein in said compound of formula I, $R^4$ is cyclopropyl and m is 1.

11. The method set forth in claim 1, wherein in said compound of formula I, $R^4$ is methoxy and m is 2.

12. The method set forth in claim 1, wherein in said compound of formula I, $R^4$ is a tetrahydrofuryl or 1,3-dioxolanyl group.

* * * * *